(12) United States Patent
Rochat et al.

(10) Patent No.: US 7,141,554 B2
(45) Date of Patent: *Nov. 28, 2006

(54) METHOD OF TREATING IRRITABLE BOWEL SYNDROME

(75) Inventors: Florence Rochat, Montreux (CH); Olivier Ballevre, Lausanne (CH); Alfred Jann, Publier (FR)

(73) Assignee: Nestec S.A., Vevey (CH)

( * ) Notice: Subject to any disclaimer, the term of this patent is extended or adjusted under 35 U.S.C. 154(b) by 1 day.

This patent is subject to a terminal disclaimer.

(21) Appl. No.: 10/942,722

(22) Filed: Sep. 16, 2004

(65) Prior Publication Data

US 2005/0053641 A1    Mar. 10, 2005

Related U.S. Application Data

(60) Division of application No. 10/350,092, filed on Jan. 24, 2003, now abandoned, which is a continuation of application No. PCT/EP01/08283, filed on Jul. 17, 2001.

(30) Foreign Application Priority Data

Jul. 24, 2000    (EP)    ................................. 00115850

(51) Int. Cl.
    *A61K 31/715*    (2006.01)
    *A61K 47/00*    (2006.01)

(52) U.S. Cl. ............................. 514/54; 514/2; 514/560; 514/23; 514/21; 514/78; 424/439; 424/757; 426/2; 426/282; 426/548; 426/549; 536/4.1

(58) Field of Classification Search ................. 514/54, 514/2, 560, 23, 21, 78; 424/459, 757; 426/2, 426/282, 548, 549, 565, 594; 536/4.1
See application file for complete search history.

(56) References Cited

U.S. PATENT DOCUMENTS

| 5,444,054 | A  | * | 8/1995 | Garleb et al. ................. 514/54 |
| 5,721,004 | A  |   | 2/1998 | James ........................ 426/573 |
| 5,792,754 | A  |   | 8/1998 | Green et al. ................. 514/60 |
| 6,197,361 | B1 | * | 3/2001 | Anantharaman et al. ..... 426/560 |
| 6,596,332 | B1 | * | 7/2003 | Anantharaman et al. ..... 426/560 |

FOREIGN PATENT DOCUMENTS

| EP | 0 756 828 A1 | 2/1997 |
| EP | 0 850 569 A1 | 7/1998 |

OTHER PUBLICATIONS

Gibson, F. R. et al., "Dietary Modulation of The Human Colonic Microbiota: Introducing the concept of Prebiotics" Journal of Nutrition, Wistar Institute Of Anatomy and Biology, Philadelphia, vol. 125, No. 6, pp. 1401-1412 (1995).

* cited by examiner

*Primary Examiner*—Shaojia Anna Jiang
*Assistant Examiner*—Devesh Khare
(74) *Attorney, Agent, or Firm*—Bell, Boyd & Lloyd LLC

(57) ABSTRACT

A nutritional composition is disclosed which comprises synergistic functional carbohydrates for preventing or treating infection by pathogenic bacteria and/or promoting gut flora balance and health. The carbohydrates have a synergistic activity on promoting bifidobacteria in the intestine. Also disclosed are a method of production of the composition; and a method of treatment of infection by pathogenic bacteria and/or promoting gut flora balance and health which comprises administering an effective amount of the composition.

17 Claims, 1 Drawing Sheet

Figure 1

Figure 1:
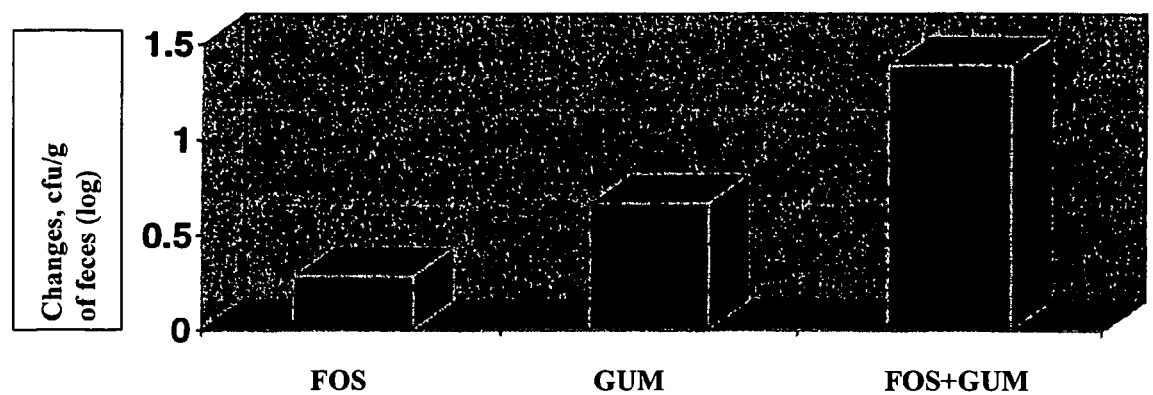

Effect of various CHO or blend on fecal bifidobacteria in man

Effect of various CHO or blend on fecal bifidobacteria in man

METHOD OF TREATING IRRITABLE BOWEL SYNDROME

CROSS-REFERENCE TO RELATED APPLICATIONS

This application is a divisional of the U.S. patent application Ser. No. 10/350,092, filed Jan. 24, 2003, which is a continuation of the U.S. national phase designation of International application PCT/EP01/08283, filed Jul. 17, 2001, the entire contents of both of which are expressly incorporated herein by reference thereto.

BACKGROUND ART

The present invention relates to a nutritional composition which comprises synergistic functional carbohydrates for prevention or treatment of infection by pathogenic bacteria and/or promoting gut flora balance and health; a method of production of the composition; and a method of treatment of infection by pathogenic bacteria and/or promoting gut flora balance and health which comprises administering an effective amount of the composition.

It has been suggested that there are health benefits associated with growth of bifidobacteria populations in the gut. These benefits include increased defense against pathogenic bacteria, stimulation of the immune system, and health benefits relating to the production of short chain fatty acids (SCFAs), as well as less abdominal sensation. All of these influence gut flora balance and gut health.

It is well known that infection by pathogenic bacteria can be detrimental to health. Examples of these bacteria include *Clostridium perfringens, C. difficile, Salmonella* and other enteropathogens.

In the past, infection by these harmful bacteria has been allowed to proceed until it must be treated by antibiotics. The antibiotics have a good effect on harmful bacteria. However, they suffer from the problem that they also kill populations of intestinal bacteria that are not harmful and that aid digestion of food. These bacterial populations are often referred to as "friendly."

Therefore, a need exists for a composition that is capable of preventing or combating infection by pathogenic bacteria, increasing defense against pathogenic bacteria, stimulating the immune system, and/or increasing short chain fatty acid production, all of which lead to promotion of gut flora balance and health.

The present invention addresses the problems set out above.

SUMMARY OF THE INVENTION

Remarkably, it has now been found that specific functional carbohydrates are capable of having a synergistic effect on the growth of bifidobacteria populations in vitro and in vivo in the gut.

Consequently, in one aspect, the present invention provides a method of treating Irritable Bowel Syndrome (IBS) in a patient in need of such treatment. The method comprises administering to the patient a nutritional composition comprising at least two synergistic functional carbohydrates, wherein a first carbohydrate is inulin or fructooligosaccharide (FOS) and a second carbohydrate is xylooligosaccharide (XOS), acacia gum or resistant starch. Advantageously, the carbohydrates are present in amounts effective to stimulate intestinal bifidobacteria, and the composition is administered in an amount effective to treat IBS by providing increased amounts of intestinal bifidobacteria.

The carbohydrates may be obtained commercially or more simply by the use of a natural source (e.g., chicory as source of inulin). The first and the second carbohydrates may be provided in a weight ratio of 1–20:0.1–20.

Further, the nutritional composition may be combined with a food, food-forming, beverage, or beverage-forming component to formulate an edible composition. The edible composition may be provided in the form of a powder or liquid concentrate, and may further comprise a fat source, such as a vegetable fat or animal fat, that provides about 5–55% of the energy of the edible composition. The edible composition may further comprise one or more of a protein source, a fat source, an additional carbohydrate source, an additional dietary fiber, a vitamin, a mineral or a food grade emulsifier. The first carbohydrate in the edible composition may be present in an amount of about 1 to 20 g, and the second carbohydrate may be present in an amount of about 0.1 to 20 g.

The present method can also be used to treat infection by pathogenic bacteria or to promote gut flora balance and health by administering an amount of the nutritional composition that is effective to stimulate intestinal bifidobacteria and thus to promote associated health benefits. The nutritional composition can also be administered in an amount effective to reduce side effects of consuming fiber.

BRIEF DESCRIPTION OF THE DRAWING FIGURES

FIG. 1 shows the effect of various carbohydrates or blends thereof on fecal bifidobacteria in human.

DETAILED DESCRIPTION OF THE PREFERRED EMBODIMENTS

Within the context of this specification the expression "side effects" is taken to mean undesirable effects often occurring after consumption of fiber. These side effects include, for example, flatulences, bloating and intestinal pain.

In humans and animals the bifidobacteria population is not the same from one individual to another and often comprises several different species of bifidobacteria. According to the present invention it is possible to stimulate specifically the growth of intestinal bifidobacteria or other lactic acid bacteria by the use of specific nondigestible carbohydrates (fiber or fiber-like substances), in vivo and in vitro.

The bifidobacteria enzymes implicated in the fermentation of embodiments of a composition according to the present invention are not identical depending on the physical and chemical structures of the carbohydrates. In addition, the bifidobacteria are not similar with regard to their enzymatic capacity, e.g., the ability to ferment one fiber or another.

Thus, a nutritional composition according to the invention which comprises a mixture of two carbohydrates or more promotes the growth of more bifidobacteria species than a single carbohydrate does. Surprisingly, a synergy exists between carbohydrates (examples of which include: fructooligosaccharides, galacto-oligosaccharide, soybean-gum, gum, starch) on the stimulation of bifidobacteria and their health benefits.

Preferably, one embodiment of the nutritional composition according to the present invention comprises fructooligosaccharide and a carbohydrate selected from the group which consists of xylooligosaccharide and acacia gum. More preferably, it comprises fructooligosaccharide and acacia gum.

Another embodiment of the nutritional composition according to the present invention comprises about 1 g to about 20 g of a first carbohydrate and about 0.1 to about 20 g of a second carbohydrate. More preferably, it comprises about 1 g to about 3 g of a first carbohydrate and about 0.2 g to about 3 g of a second carbohydrate for an infant, and about 2 g to about 5 g of a first carbohydrate and about 2 g to about 5 g of a second carbohydrate for an adult, although it will be apparent that there are no specific limitations except for what can reasonably be consumed and the price. The amounts given correspond to a daily dose, which may be divided into several servings in one day, if desired.

In yet another embodiment, a ratio by weight of the first and the second functional carbohydrate is 1–20:0.1–20. More preferably, it is between 0.05–10:1, even more preferably, between 0.1–10:1.

The invention also provides an edible composition formulated for human consumption and/or administration. This composition includes a food, food-forming, beverage, or beverage-forming component and one of the nutritional compositions of the invention. An alternative embodiment of this edible composition is formulated for consumption by a companion animal.

One advantage of the present invention is that it provides a composition that can be provided in a functional food product and which therefore does not require special administration.

Another advantage of the present invention is that it does not adversely kill or affect non-harmful intestinal bacteria.

Yet another advantage of the present invention is that it provides a decrease of the daily amount of carbohydrates required in the gut to obtain stimulation of intestinal bifidobacteria and for the promotion of the associated health benefits. The benefits that this decrease provides include reduction of the side effects (abdominal disturbance) induced by the intake of some fermentable carbohydrates, and in some cases a reduction in cost.

Yet another advantage of the present invention is that it provides a composition of carbohydrates having various lengths of carbohydrate chains. This enables modulating fermentation throughout the colon as the composition passes through it.

Additional features and advantages of the present invention are given below. Comparative data showing results in human studies of using fructooligosaccharides plus acacia gum or plus xylo-oligosaccharides are given in the Examples. The data demonstrate a greater increase of bifidobacteria with a synergistic mix of carbohydrates than with single carbohydrate. These examples are described below.

In an embodiment, the nutritional composition preferably comprises a source of protein. Dietary protein is preferred as a source of protein. The dietary protein may be any suitable dietary protein, for example an animal protein (such as milk protein, meat protein or egg protein); a vegetable protein (such as soy protein, wheat protein, rice protein, and pea protein); a mixture of free amino acids; or a combination thereof. Milk proteins such as casein, whey proteins and soy proteins are particularly preferred.

The composition may also comprise a source of fat. If the nutritional formula includes a fat source, the fat source preferably provides about 5% to about 55% of the energy of the nutritional formula; more preferably about 20% to about 50% of the energy. Lipids making up the fat source may be any suitable fat or fat mixture. Vegetable fat is particularly suitable, for example, soy oil, palm oil, coconut oil, safflower oil, sunflower oil, corn oil, canola oil, lecithins, and the like. Animal fat such as milk fat may also be added if desired.

An additional source of carbohydrate may be added to the nutritional composition. It preferably provides about 40% to about 80% of the energy of the nutritional composition. Any suitable carbohydrate may be used, for example, sucrose, lactose, glucose, fructose, corn syrup solids, maltodextrin, or a mixture thereof.

Additional dietary fiber may also be added if desired. If added, it preferably comprises up to about 5% of the energy of the nutritional composition. The dietary fiber may be from any suitable origin, including, for example, soy, pea, oat, pectin, guar gum, acacia gum, fructooligosaccharide or a mixture thereof.

Suitable vitamins and minerals may be included in the nutritional composition in an amount to meet the appropriate guidelines.

One or more food grade emulsifiers may be included in the nutritional composition if desired, for example, diacetyl tartaric acid esters of mono- and di-glycerides, lecithin and mono- or di-glycerides or a mixture thereof. Similarly, suitable salts and/or stabilizers may be included.

The nutritional composition is preferably enterally administrable, for example, in the form of a powder, a liquid concentrate, or a ready-to-drink beverage. If it is desired to produce a powdered nutritional formula, the homogenized mixture is transferred to a suitable drying apparatus such as a spray drier or freeze drier and converted to powder.

Alternatively, a common food product may be enriched with an embodiment of the composition. For example, a milk, such as a fermented milk, a yogurt, a fresh cheese, or a renneted milk, may be provided with the nutritional composition of the invention. The food product may also be a confectionery bar, breakfast cereal flakes or bars, a drink, milk powder, soy-based product, non-milk fermented product or a nutritional supplement for clinical nutrition, infant formulae or baby food. In these situations, the amount of the composition added is preferably at least about 0.01% by weight.

An embodiment of the composition may be included in an article of confectionery, for example a sweet or sweetened beverage.

EXAMPLES

The following examples are given by way of illustration only and in no way should be construed as limiting the subject matter of the present application. Percentages and parts are by weight unless otherwise indicated.

Example 1

A parallel design, consisting of 3 groups of 29 volunteers each, has been used:
FOS: 6 g daily of (Raftilose P95N) during 6 weeks.
XOS: 0.4 g daily of Xylo-oligo P95 during 6 weeks
XOS FOS: 4 g daily of FOS and 0.2 g daily of XOS, during 6 weeks Before the 6 weeks of treatment, a wash-out period of 3 weeks was observed. The participants were then followed-up during 5 additional weeks after the end of the treatment. During the wash-out and follow-up periods, the volunteers received a placebo.

During the complete test period, subjects refrained from eating fermented yogurts and products containing bifidus.

In general the test subjects showed an increase of bifidobacteria counts, particularly those who had a low initial value. The average and median increases were also calculated. A formal statistical analysis, shown below in Table I, gave the following results:

TABLE 1

Differences of bifidobacteria counts between start and first week of treatment

|  | start | +1 week | Difference | p-value |
|---|---|---|---|---|
| FOS [$\log_{10}$ cfu/g] | | | | |
| Mean (t-test) | 8.41 | 9.02 | +0.61 | 0.019 |
| XOS [$\log_{10}$ cfu/g] | | | | |
| Mean (t-test) | 7.43 | 8.11 | +0.68 | 0.042 |
| XOS FOS [$\log_{10}$ cfu/g] | | | | |
| Mean (t-test) | 7.39 | 8.85 | +1.45 | <0.001 |

The results shown in the table provide clear indicate that FOS and XOS FOS significantly increase the average bifidobacteria counts. This is also the case for XOS, but to a lesser extent. The increase obtained with the mixed XOS FOS is synergistically higher.

Example 2

The trial was designed, according to the protocol, to compare three groups of 32 resp. 31 subjects in parallel:

FOS: 200 ml of skimmed milk with Raftilose P95®, 6 g per serving.

Fibergum: 200 ml of skimmed milk with Fibergum AS IRX®, 6 g per serving.

FOS+Fibergum: 200 ml of skimmed milk with Raftilose P95® (3 g per serving) and Fibergum TX® (3 g per serving).

Feces samples were tested 7, 21, 28, 49 and 71 days after the start of the study. The intervention period is between day 21 and 49. The change from day 21 to day 28 is of particular interest.

According to the protocol, a +1.35 $\log_{10}$ cfu/g of feces increase of Bifidobacteria after one week of treatment is expected for the FOS+Fibergum group.

The individual changes in the FOS+Fibergum group from day 21 to day 28 are summarized below:

| Min. | 1st Qu. | Mean | 3rd Qu. | Max. |
|---|---|---|---|---|
| −0.33 | 0.07 | 1.384 | 1.42 | 6.73 |

The differences were analyzed in two ways, first from a quantitative point of view, then more from a qualitative point of view.

Use of a robust location estimator, for example the M-estimator using Turkey's bisquare function gave an "average" of 0.307 $\log_{10}$ cfu/g of feces, close to the median value. A 95% confidence interval was calculated by bootstrapping 1000 times (this is why the M-estimator was preferred compared to the median in this case). This gave as limits 0.14 and 1.00, that is an interval which does not include the value 0, indicating that the increase was statistically significant.

The "responders" were determined with the criteria of an increase of at least +0.5 $\log_{10}$ cfu/g of feces. This was observed for 13 out of 29 subjects, which represented 44.8% of the volunteers. A 95%-confidence interval for this proportion was from 27 to 64%. We could say that at least 27% of the subjects responded to the diet provided, and it could be as high as 64%.

Using both approaches, significant results were obtained.

For the Fibergum group, we obtained the following differences:

| Min. | 1st Qu. | Mean | 3rd Qu. | Max. |
|---|---|---|---|---|
| −6.26 | 0 | 0.6678 | 0.875 | 6.6 |

Here, median and mean differences were closer, and a t-test was appropriate. The average increase was at the limit of statistical significance (p-value=0.09, 95%-C1: [−0.11, 1.45]).

Finally, for the FOS group, the differences were distributed as follows:

| Min. | 1st Qu. | Mean | 3rd Qu. | Max. |
|---|---|---|---|---|
| −4.04 | 0.0625 | 0.2853 | 0.655 | 4.31 |

Example 3

100 volunteers were assigned randomly to 4 diet groups, but stratified for their amount of native intestinal Bifidobacteria before the trial based on gender, age and average portions of fiber in the daily diet. The 4 diet groups are described below:

| Control | Reference Product |
|---|---|
| FOS + GUM | Raftilose ® 3 g and Fibergum 3.56 g per serving |
| Starch | Resistant Starch 10 g per serving |
| Blend | Raftilose ® 3 g + Fibergum 3.56 g + Resistant Starch 10 g per serving |

The primary analysis as to the outcome is the effect on the amount of Bifidobacteria in the feces. Counts of other micro-organisms were also analyzed. A further analysis was carried out to determine changes of abdominal sensation (flatulencies, quality and number of stools) as assessed by the volunteers, followed by an analysis of several short chain fatty acids measured in the feces.

The 100 volunteers were allocated to 4 groups as follows:

| Control: | 13 subjects (8 females, 5 males) |
|---|---|
| FOS + GUM: | 29 subjects (19 females, 10 males) |
| Starch: | 29 subjects (19 females, 10 males) |
| Blend: | 29 subjects (19 females, 10 males) |

Their average amounts of bifidobacteria, ages and portions of fiber were similar. There was one subject who clearly was not in compliance (Group "FOS+GUM"), and its data were omitted.

It was set out to demonstrate that after 4 weeks of treatment, 50% of the subjects showed an increase of at least +0.5 $\log_{10}$ cfu/g of bifidobacteria in feces. The lower boundaries of a 95%-Confidence Interval (CI) for the estimated proportion should be above 25%.

For the duration "Day 20 to Day 48", the following results were obtained of $\log_{10}$ cfu bifidobacteria/g feces (p) in (n) number of people. The number of people having at least 0.5 $\log_{10}$ cfu/g is shown in the first column (+0.5).

| | Bifidobacteria: | | | |
| | Day 48 minus day 20 | | | |
| | +0.5 | n | p | Lower | Upper |
| --- | --- | --- | --- | --- | --- |
| Control | 3 | 13 | 23.1 | 6.2 | 54.0 |
| FOS + GUM | 9 | 27 | 33.3 | 17.2 | 54.0 |
| Starch | 7 | 27 | 25.9 | 11.9 | 46.6 |
| Blend | 13 | 27 | 48.1 | 29.2 | 67.6 |

In the above table, we see that, in the Control group, there were 3 out of 13 subjects that have an increase of at least 0.5 $\log_{10}$ cft/g of feces. This represents 23.1%, with a 95%-confidence interval (CI) ranging from 6.2% up to 54.0%. For the Blend, the proportion was close to 50%, and the lower boundary of the 95%-CI is above 25%. Clearly there was a significant effect after 4 weeks of consuming the blend.

After 1 week, the following results were obtained:

| | Bifidobacteria: | | | |
| | Day 27 minus day 20 | | | |
| | +0.5 | n | p | Lower | Upper |
| --- | --- | --- | --- | --- | --- |
| Control | 5 | 13 | 38.5 | 15.1 | 67.7 |
| FOS + GUM | 12 | 28 | 42.9 | 25.0 | 62.6 |
| Starch | 9 | 28 | 32.1 | 16.6 | 52.4 |
| Blend | 11 | 29 | 37.9 | 21.3 | 57.6 |

Here, the effect of FOS+GUM was significant, and the blend was at the limit of statistical significance.

Changes in the amount of bifidobacteria were checked after 1 and 4 weeks of treatment to assess whether they related to the average portions of fiber eaten per subject. No striking association was found.

Similar experiments were carried out to determine the amounts of lactobacilli, bacteroides, enterobacteria and clostridium per fingens. It was surprisingly found that the number of these bacteria did not change significantly with respect to the different diets. This demonstrated the surprising result that an embodiment of the invention has the effect of specifically enhancing bifidobacteria. This result positively affects digestion, combats infection by pathogenic bacteria, stimulates the immune system, increases short chain fatty acid production and leads to promotion of gut flora balance and health.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be encompassed by the appended claims.

What is claimed is:

1. A method of treating Irritable Bowel Syndrome (IBS) in a patient in need of such treatment, which comprises administering thereto a nutritional composition comprising at least two synergistic functional carbohydrates, wherein a first carbohydrate is inulin or fructooligosaccharide (FOS) and a second carbohydrate is xylooligosaccharide (XOS), acacia gum or resistant starch, with the carbohydrates being present in amounts effective to stimulate intestinal bifidobacteria, and the composition being administered in an amount effective to treat IBS by providing increased amounts of intestinal bifidobacteria.

2. A method according to claim 1, wherein the first carbohydrate of the nutritional composition comprises inulin and the second carbohydrate comprises an xylooligosaccharide.

3. A method according to claim 1, wherein the first carbohydrate of the nutritional composition comprises inulin and the second carbohydrate comprises acacia gum.

4. A method according to claim 1, wherein the first carbohydrate comprises fructooligosaccharide and the second carbohydrate comprises an xylooligosaccharide.

5. A method according to claim 1, wherein the first carbohydrate comprises fructooligosaccharide and the second carbohydrate comprises acacia gum.

6. A method according to claim 1, wherein the first and the second carbohydrates are present in the composition in a weight ratio of 1–20:0.1–20.

7. A method according to claim 1, wherein the nutritional composition is combined with a food, food-forming, beverage, or beverage-forming component to formulate an edible composition that is administered to the patient.

8. A method according to claim 7, wherein the edible composition is in the form of a powder or liquid concentrate.

9. A method according to claim 7, wherein the first carbohydrate is present in an amount of about 1 g to about 20 g and the second carbohydrate is present in an amount of about 0.1 g to about 20 g.

10. A method according to claim 7, wherein the first and the second carbohydrates are present in a weight ratio of 1–20:0.1–20.

11. A method according to claim 7, wherein the edible composition further comprises a fat source that provides about 5% to about 55% of the energy of the edible composition.

12. A method according to claim 11, wherein the fat source is a vegetable fat or animal fat.

13. A method according to claim 7, wherein the edible composition further comprises one or more of a protein source, a fat source, an additional carbohydrate source, an additional dietary fiber, a vitamin, a mineral or a food grade emulsifier.

14. A method according to claim 7, wherein the edible composition further contains milk.

15. A method according to claim 1, wherein the composition is administered in an amount sufficient to treat an infection by pathogenic bacteria.

16. A method according to claim 1, wherein the composition is administered in an amount sufficient to promote gut flora balance and health in the patient.

17. A method according to claim 1, wherein the composition is administered in an amount sufficient to reduce side effects of consuming fiber by the patient.

* * * * *